United States Patent [19]

Byrne, Jr.

[11] Patent Number: 5,257,420
[45] Date of Patent: Nov. 2, 1993

[54] EARMUFFS FOR USE WITH HEADPHONES

[75] Inventor: Richard J. Byrne, Jr., Brooklyn, N.Y.

[73] Assignee: Hearz, Inc., Brooklyn, N.Y.

[21] Appl. No.: 923,052

[22] Filed: Jul. 31, 1992

[51] Int. Cl.5 .............................................. A42B 1/06
[52] U.S. Cl. ........................................... 2/209; 2/423
[58] Field of Search ................. 2/208, 209, 209.1, 422, 2/423, DIG. 11

[56] References Cited

U.S. PATENT DOCUMENTS

| | | | |
|---|---|---|---|
| 1,555,928 | 10/1925 | Morrissey | 2/209 |
| 4,243,851 | 1/1981 | Forney | 2/423 |
| 4,459,707 | 7/1984 | Stallings | 2/208 |
| 4,546,215 | 10/1985 | Ferraro | 2/209 |
| 4,669,129 | 6/1987 | Chance | 2/209 |
| 4,776,044 | 10/1988 | Makins | 2/209 |
| 4,858,248 | 8/1989 | Goldsmith | 2/209.1 |

FOREIGN PATENT DOCUMENTS 2538204 6/1984 France .................................... 2/209

Primary Examiner—Clifford D. Crowder
Assistant Examiner—Diana L. Biefeld
Attorney, Agent, or Firm—Collard & Roe

[57] ABSTRACT

Earmuffs for use with headphones of the type having two speakers connected by a headband including two speaker receiving pouches. A headband receiving pouch is connected between the two speaker receiving pouches. Closing means are provided for closing the two speaker receiving pouches around the two speakers and for closing the headband receiving pouch around the headband. The two speaker receiving pouches can warm a listener's ears while using headphones.

4 Claims, 3 Drawing Sheets

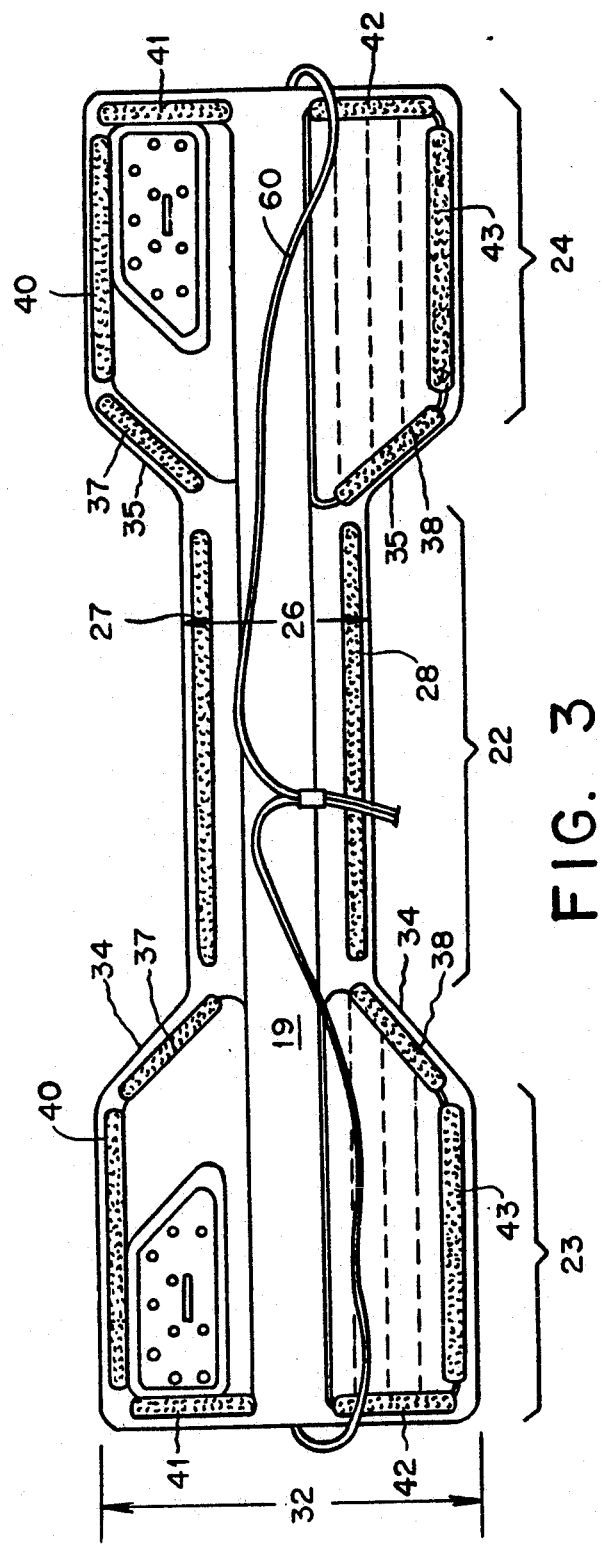
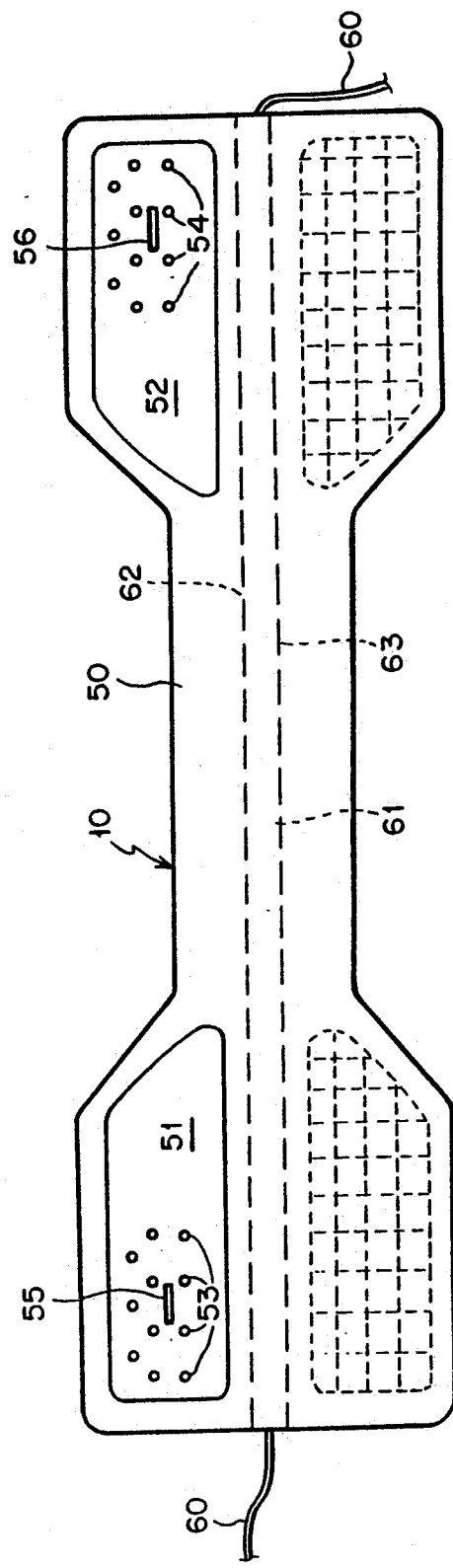
FIG. 3
FIG. 4

EARMUFFS FOR USE WITH HEADPHONES

BACKGROUND OF THE INVENTION

1. Field of the Invention

The present invention relates to earmuffs for use with headphones. More specifically, it relates to earmuffs having pouches for receiving the headphones and keeping an individual's ears warm while listening to headphones.

2. The Prior Art

Headphones are known which have a miniature speaker portion for each ear and a headband connecting the two speaker portions together. The headband extends from one ear over the top of a listener's head to the other ear to hold the speakers adjacent to the listener's ears. Battery power portable tuners/tape decks/CD players are known which allow an individual to listen to music through headphones while running or walking outdoors. However, a significant drawback exists in that during the cold weather, earmuffs which also include a headband cannot be worn with headphones because the headbands would interfere with each other. In addition, for earmuffs to be effective, they generally press tightly against an individual's ears, which would be painful if the headphone speakers were located between the earmuffs and the ear. As a result, an individual who wishes to run or walk outdoors during cold weather must choose between wearing headphones or earmuffs, or else experience significant discomfort by wearing both.

SUMMARY OF THE INVENTION

It is therefore an object of the present invention to provide an earmuff for use with headphones which overcomes the drawbacks of the prior art and keep an individual's ears warm while listening to a pair of headphones.

It is a further object of the present invention to provide an earmuff for use with headphones which will not interfere with the sound emanating from the headphone speakers.

These and other related objects are achieved according to the invention by an earmuff for use with headphones of the type having two speakers connected by a headband. The earmuff includes two speaker receiving pouches and a headband receiving pouch connected between the two speaker receiving pouches. Closing means are provided for closing the two speaker receiving pouches around the two speakers and for closing the headband receiving pouch around the headband. The two speaker receiving pouches can warm a listener's ears while using headphones.

Alternatively, the earmuffs can be used with headphones of the type having a headband and miniature speakers which are placed into the outer ear canal. For this purpose, the speaker receiving pouches include a slit adjacent to the ears. The miniature speakers pass through the slits so that the speakers can be placed within the ears while the ears remain covered.

BRIEF DESCRIPTION OF THE DRAWINGS

Other objects and features of the present invention will become apparent from the following detailed description considered in connection with the accompanying drawings which disclose an embodiment of the present invention. It should be understood, however, that the drawings are designed for the purpose of illustration only and not as a definition of the limits of the invention.

In the drawings, wherein similar reference characters denote similar elements throughout the several views:

FIG. 3 is a front side elevational view of the earmuffs fully opened;

FIG. 4 is a backside elevational view of the earmuffs; and

DETAILED DESCRIPTION OF THE PREFERRED EMBODIMENT

Figure 1:
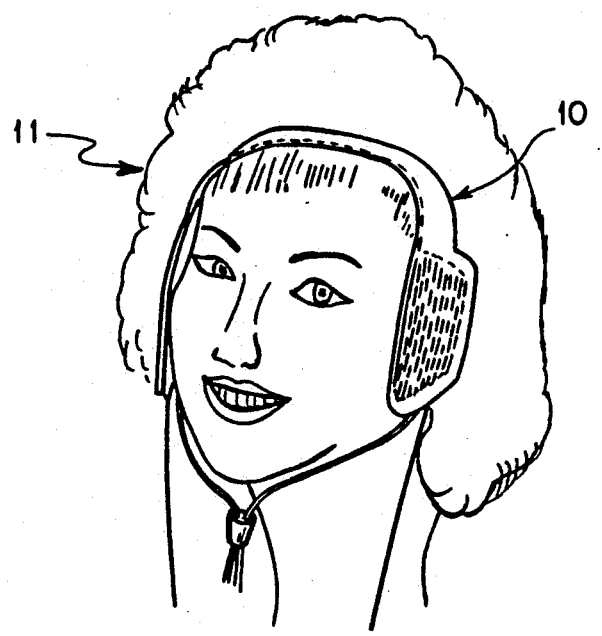
FIG. 1 is a perspective view of earmuffs for use with headphones, according to the invention, shown in use on an individual's head.
Figure 2:
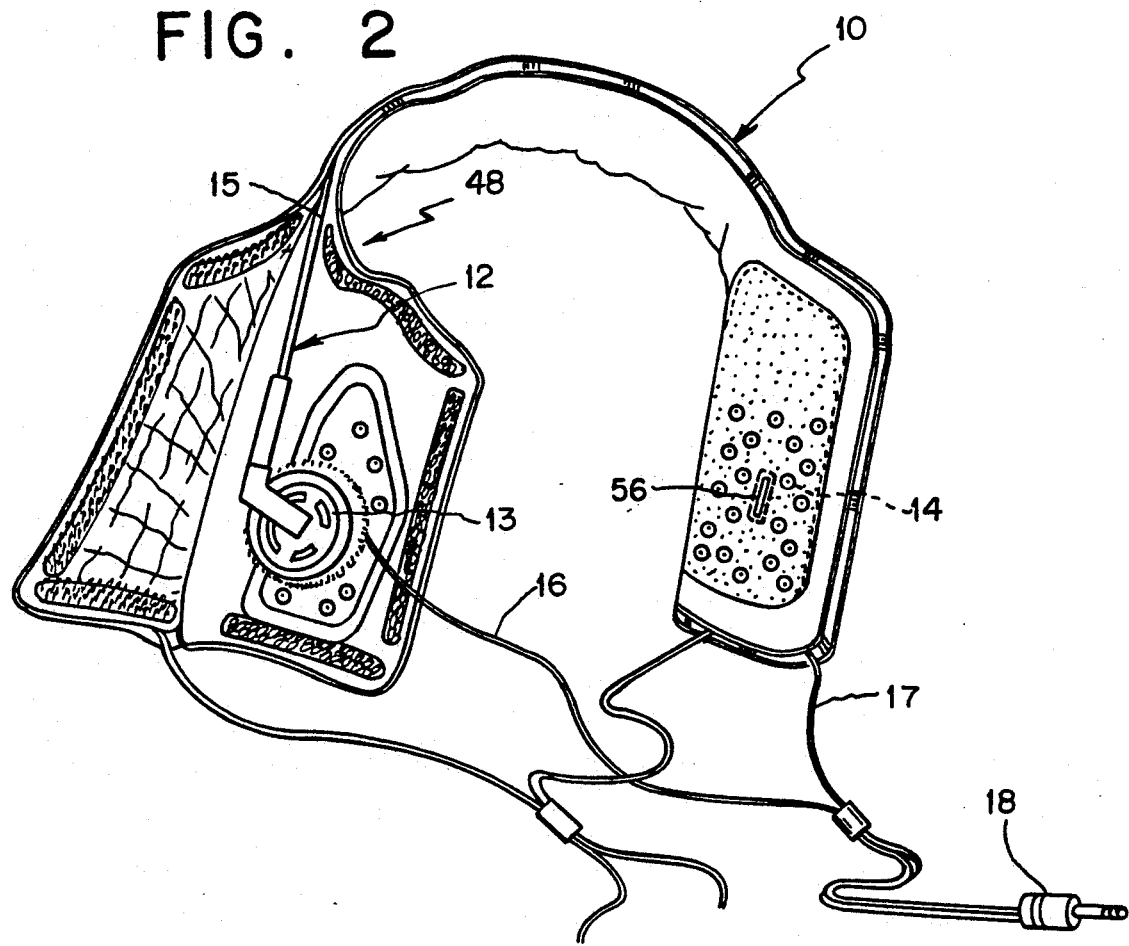
FIG. 2 is a perspective view of the earmuffs with one side partially open showing the headphones.

Referring now to the drawings and, in particular, to FIG. 1, there is shown earmuffs 10 for use with headphones according to the present invention shown on a listener's head 11. As can be seen in FIG. 2, earmuffs 10 fit over headphones 12 which include miniature speakers 13 and 14 and headband 15. Speakers 13 and 14 are coupled to a portable tuner/tape deck/CD player by wires 16 and 17, respectively. Wires 16 and terminate in a single stereo jack 18.

FIG. 3 shows inner surface 19 of earmuffs 10 including a central region 22 and end flaps 23 and 24. Central region or headband receiving pouch 22 has a width 26 which is wide enough to wrap completely around headband 15. Along the edges of central region 22 are located strips of male and female interlocking materials. For example, strip 27 may be the hook portion of a hook and loop fastener, while strip 28 may be the loop portion of a hook and loop fastener. Central region 22 is wrapped around headband 15 and strips 27 and 28 are interlocked to completely enclose headband 15 and provide a cushion between headband 15 and the listener's head 11. End flaps 23 and 24 are generally rectangular or square shaped and have a width 32 which is approximately twice as wide as width 26. Central region 22 extends into endflaps 23 and 24 by intermediate regions 34 and 35 which are trapezoidally shaped. Along the edges of intermediate regions 34 and 35, there are strips 37 and 38, of male and female interlocking materials. For example, strips 37 can be the hook portion of a hook and loop fastener while strip 38 is the loop portion of a hook and loop fastener, for example, as sold under the trademark Velcro ®. Other closing or fastening means may be employed with the device according to the invention, for example, snaps or zippers, etc.

Also, along the perimeter of endflaps 23 and 24, there are strips 40, 41, 42 and 43 of male and female interlocking material. For example, strip 40 and 41 can be the hook portion of a hook and loop fastener, while strips 42 and 43 can be the loop portion of a hook and loop fastener. Intermediate regions 34 and 35 flare outwardly to meet endflaps 23 and 24. Intermediate regions 34 and 35 and endflaps 23 and 24 cooperatively provide a large pocket 48 which can be seen in FIG. 2. Pocket or pouch 48 encloses speaker 13 and a lower portion of headband 15 which attaches to speaker 13. When earmuffs 10 are fully closed, headband 15 and speakers 13 and 14 are fully enclosed, for example, as shown in FIG. 1.

Figure 5:
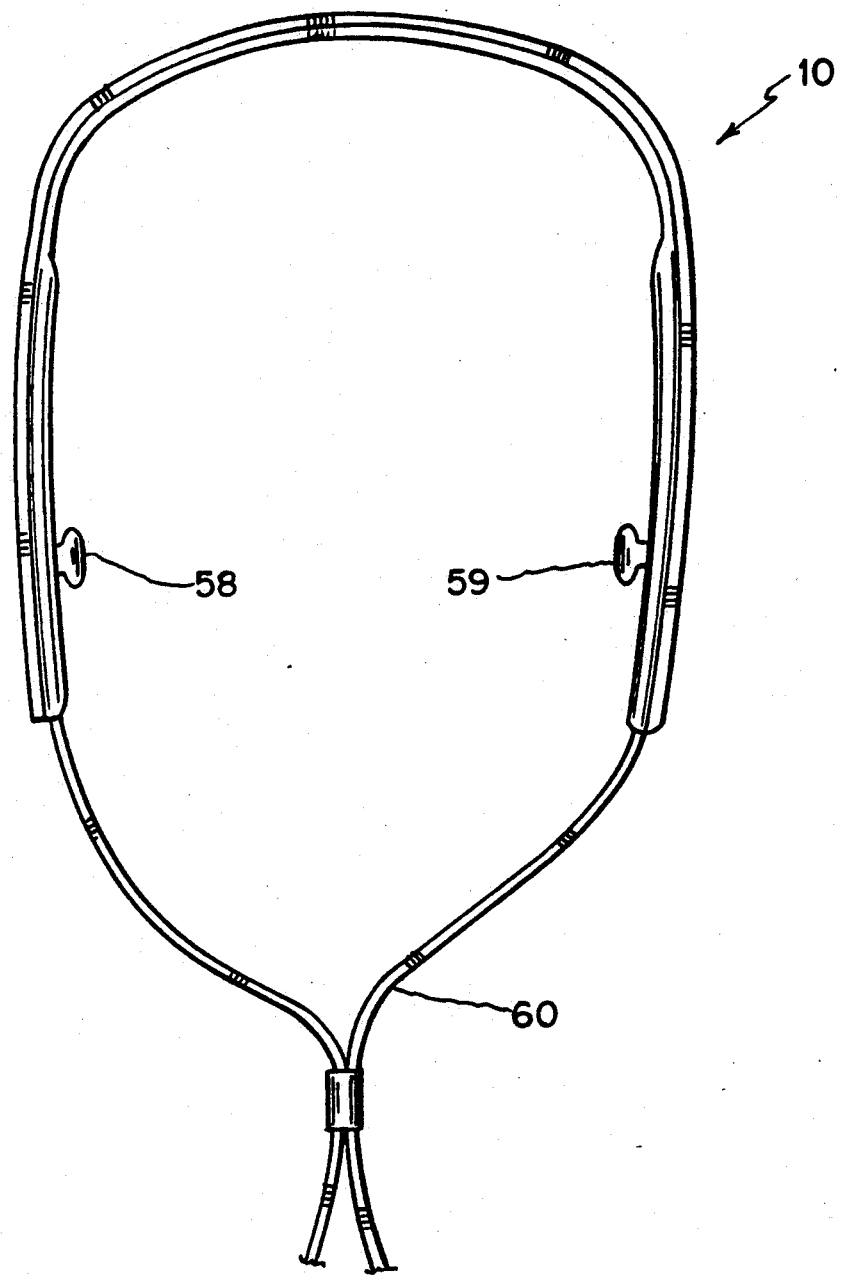
FIG. 5 is a front side elevational view of the earmuffs closed.

FIG. 4 shows outer surface 50 having earflaps 51 and 52 which, in use, would be located between speakers 13 and 14 and the listener's ears. Earmuffs 10 may be made from a variety of natural or artificial fibers, for example, cotton, nylon, polyester, sheepskin, etc. Earflaps 52 and 51 which are next to the listener's ears can be made of a soft material, for example, cotton, while the remainder of the earmuffs can be made of a thicker, insulating material, for example, lined polyester. Earflaps 52 and 51 are each provided with a plurality of perforations 53 and 54 which provide a clear path for the signal emanating from speakers 13 and 14. Amongst the plurality of holes 53 and 54 are two elongated slits 55 and 56 through which miniature speakers may pass through. These miniature speakers may be of a type which are placed directly into the outer ear canal. As can be seen in FIG. 5, slit 56 is located adjacent to the ear, so that in use, miniature speakers 58 and 59 may pass through slits 56 and be placed into the outer ear canal.

Also, as can be seen in FIGS. 3 and 4, earmuffs 10 include a drawstring 60 which passes through a narrow slit 61 which passes through the length of earmuffs 10. Narrow slit 61 is formed by an opening which is bordered by two lines of stitching 62 and 63 which extend lengthwise across earmuffs 10. Drawstring 60, as can be see in FIG. 1, extends out of the ends or side of earmuffs 10 for passing underneath the chin or behind the head of the listener. Drawstring 60 can be tightened to secure the earmuffs to the listener's head.

While only a single embodiment of the present invention has been shown and described, it is to be understood that many changes and modifications may be made thereunto without departing from the spirit and scope of the invention as defined in the appended claims.

What is claimed is:

1. Earmuffs for use with headphones of the type having two speakers connected by a headband comprising:

two speaker receiving pouches including listening panels made of flexible material located between the speakers and the listener's ears, said listening panels including openings therein to provide a clear path for the sound emanating from the speakers to the listener's ears;

a headband receiving pouch connected between said two speaker receiving pouches, said headband receiving pouch having a length approximately equal to the length of the headband, and having a width approximately equal to one-half the width of said two speaker receiving pouches, wherein said earmuffs are generally I-shaped;

two trapezoidally-shaped receiving pouches, each having a base and a top parallel to said base, and wherein said two speaker receiving pouches are generally rectangular shaped and are connected to said base of said trapezoidally-shaped receiving pouch, and said headband receiving pouch is connected to said top of said trapezoidally-shaped receiving pouch; and means for closing said two speaker receiving pouches around the two speakers and for closing said headband receiving pouch around the headband so that said two speaker receiving pouches can warm a listener's ears while using headphones.

2. The earmuffs according to claim 1, wherein said means for closing additionally closes said two trapezoidally-shaped receiving pouches around the headband in the region of the two speakers.

3. The earmuffs according to claim 2, additionally including a drawstring passing through a narrow slit located within said two speaker receiving pouches, said headband receiving pouch and said trapezoidally-shaped receiving pouches, said drawstring passing around the head of the listener to secure the earmuffs to the listener.

4. The earmuffs according to claim 3, wherein said two speaker receiving pouches include slits adjacent to the listener's ears, and the speakers are miniature speakers connected by a headband intended to be placed into the outer ear canal, whereas the miniature speakers pass through the slits so that the miniature speakers can be placed into the outer ear canal.

* * * * *